(12) United States Patent
Weiss et al.

(10) Patent No.: US 6,342,600 B1
(45) Date of Patent: Jan. 29, 2002

(54) PROCESS FOR PREPARING 2-METHOXY-4-METHYL-6-METHYLAMINO-1,3,5-TRIAZINE

(75) Inventors: Stefan Weiss; Helmut Krommer, both of Trostberg (DE)

(73) Assignee: SKW T Ostberg Aktiengesellschaft, Trostberg (DE)

( * ) Notice: Subject to any disclaimer, the term of this patent is extended or adjusted under 35 U.S.C. 154(b) by 0 days.

(21) Appl. No.: 09/749,302

(22) Filed: Dec. 27, 2000

(51) Int. Cl.[7] ............................................. C07D 251/16
(52) U.S. Cl. ...................................................... 544/194
(58) Field of Search ........................................... 544/194

(56) References Cited

U.S. PATENT DOCUMENTS 4,933,450 A * 6/1990 Chiang ........................ 544/194

* cited by examiner

*Primary Examiner*—John M. Ford
(74) *Attorney, Agent, or Firm*—Fulbright & Jaworski, LLP

(57) ABSTRACT

Provided herein is a novel and useful process for preparing 2-methoxy-4-methyl-6-methylamino-1,3,5-triazine that broadly comprises the steps of (a) reacting zinc bis(imino-bis-carbimic acid methyl ester) with acetic anhydride to give 2,4-dimethoxy-6-methyl-1,3,5-triazine and (b) reacting the 2,4-dimethoxy-6-methyl-1,3,5-triazine, formed in step (a), with methylamine to give 2-methoxy-4-methyl-6-methylamino-1,3,5-triazine.

20 Claims, No Drawings

US 6,342,600 B1

PROCESS FOR PREPARING 2-METHOXY-4-METHYL-6-METHYLAMINO-1,3,5-TRIAZINE

FIELD OF THE INVENTION

The present invention relates to a process for preparing 2-methoxy-4-methyl-6-methylamino-1,3,5-triazine which is of great industrial importance as an intermediate for preparing plant-protective agents, in particular sulfonylurea herbicides.

BACKGROUND OF THE INVENTION

The preparation of 2-methoxy-4-methyl-6-methylamino-1,3,5-triazine by reaction of 2,4-dimethoxy-6-methyl-1,3,5-triazine with methylamine at 80° C. is known from the publication of G. Rembarz et al., Wiss. Z. Univ. Rostock, Math.-Naturwiss. Reihe 1972, 21 (2), 113–117, the yield being 80%. The 2,4-dimethoxy-6-methyl-1,3,5-triazine required as starting material can be prepared according to DD 71 768 by reaction of zinc bis(imino-bis-carbimic acid methyl ester) with acetic anhydride, the solvent used being acetic anhydride or benzene. Zinc bis(imino-bis-carbimic acid methyl ester) can be prepared in accordance with the publication of G. Rembarz et al., Journal für praktische Chemie 311, 1969, by heating zinc dicyanamide in methanol. According to DD 70 296, this intermediate is also obtained by heating sodium dicyanamide with zinc chloride in methanol, it being possible to remove the sodium chloride formed as byproduct by filtering the hot mixture.

Finally, U.S. Pat. 4,933,450 describes the preparation of zinc bis(imino-bis-carbimic acid methyl ester) by heating zinc dicyanamide in methanol in the presence of a ligand such as pyridine, triethylamine, N,N-dimethylaniline, acetonitrile or tetrahydrofuran, where the corresponding product is then reacted in excess acetic anhydride to give 2,4-dimethoxy-6-methyl-1,3,5-triazine, which is subsequently isolated by extraction with dichloromethane and finally converted into 2-methoxy-4-methyl-6-methylamino-1,3,5-triazine using methylamine in dilute aqueous solution.

However, the synthesis processes described in the prior art are unsuitable for preparing 2-methoxy-4-methyl-6-methylamino-1,3,5-triazine on an industrial scale, since they have a number of serious disadvantages. Firstly, zinc dicyanamide in solid and dried form is extremely unstable since it may decompose spontaneously in a strongly exothermic reaction—in particular on drying.

Secondly, the preparation of 2,4-dimethoxy-6-methyl-1,3,5-triazine requires the use of excess acetic anhydride or benzene as solvent. Since acetic anhydride has a relatively high boiling point of 139° C. and furthermore unpleasant product properties, it is very difficult to remove the zinc acetate formed from the acetic anhydride-containing reaction mixture and to remove the acetic anhydride by distillation. The use of benzene is likewise extremely problematic, owing to its physiological properties.

It is a further disadvantage of the known processes that, in the reaction of 2,4-dimethoxy-6-methyl-1,3,5-triazine with methylamine in aqueous solution, the reaction product is obtained in a crystal form which is poorly filterable and furthermore has a relatively high moisture content.

Finally, the 2-methoxy-4-methyl-6-methylamino-1,3,5-triazine prepared by known processes is not sufficiently pure for the preparation of the highly active sulfonylurea herbicides, since a number of other 1,3,5-triazines, such as 2-amino-4-methoxy-6-methyl-1,3,5-triazine, are formed as undesirable byproducts in the preparation.

SUMMARY OF THE INVENTION

Accordingly, it was an object of the present invention to develop a three-step process for preparing 2-methoxy-4-methyl-6-methylamino-1,3,5-triazine consisting of
  a) the preparation of zinc bis(imino-bis-carbimic acid methyl ester),
  b) subsequent reaction of the intermediate from step a) with acetic anhydride to give 2,4-dimethoxy-6-methyl-1,3,5-triazine and
  c) reaction of the 2,4-dimethoxy-6-methyl-1,3,5-triazine, formed in step b), with methylamine to give the desired end product,
which does not have the abovementioned disadvantages of the prior art but permits the preparation of 2-methoxy-4-methyl-6-methylamino-1,3,5-triazine in good yield and high purity in a manner which does not cause any problems when realized on an industrial scale.

According to the invention, this object has been achieved by preparing in step a) zinc bis(imino-biscarbimic acid methyl ester) by reaction of sodium dicyanamide with zinc acetate in methanol, then also reacting in step b) the reaction product formed in step a) in dried or methanol-moist form, with acetic anhydride at from 30 to 80° C. without addition of a solvent and finally, after removal of the byproducts from steps a) and b), converting in step c) 2,4-dimethoxy-6-methyl-1,3,5-triazine by reaction with methylamine in methanolic solution at from 0 to 30° C. into the end product.

Surprisingly, it has been found that zinc bis(iminobiscarbimic acid methyl ester) can be prepared even without using zinc dicyanamide, which is highly dangerous owing to its instability. Moreover, the acetylation of zinc bis(imino-bis-carbimic acid methyl ester) in a virtually stoichiometric amount to give 2,4-dimethoxy-6-methyl-1,3,5-triazine can be carried out in very high yields even without addition of a solvent. Finally, in this manner the desired end product can be prepared with very good yields and in high purity in crystalline, readily filterable form, which was likewise unforeseeable.

In the process of the present invention, zinc bis(imino-bis-carbimic acid methyl ester) is prepared according to step a) by reacting sodium dicyanamide and zinc acetate in methanolic solution, where sodium dicyanamide and zinc acetate are preferably employed in stoichiometric or virtually stoichiometric amounts. The molar ratio of sodium dicyanamide to zinc acetate is preferably from 2:1 to 2.1:1. The reaction of sodium dicyanamide and zinc acetate in methanolic solution is preferably carried out at from 40 to 70° C. In this manner, it is possible to avoid the preparation and isolation of zinc dicyanamide in step a).

After the reaction has ended (about 8 to 12 hours), the mixture is cooled and the zinc bis(imino-bis-carbimic acid methyl ester), which is obtained as a solid, is separated off by customary methods, such as filtration or centrifugation. In the context of the present invention, this intermediate formed in step a) can be employed for the subsequent step b) in dried or else in methanol-moist form having a methanol content of from 1 to 10% by weight, preferably 3% by weight.

In the process according to the invention, this reaction of the zinc bis(imino-bis-carbimic acid methyl ester) with acetic anhydride is carried out at from 30 to 80° C. using—in contrast to the prior art—virtually stoichiometric amounts, so that from 4.0 to 4.4 mol of acetic anhydride are employed per mol of zinc bis(imino-bis-carbimic acid methyl ester). If methanol-moist zinc bis(imino-bis-carbimic acid methyl ester) is employed for step b), one additional mol of acetic anhydride is employed per mol of methanol in the methanol-moist intermediate. According to a preferred embodiment, step b) is carried out by initially charging acetic anhydride and introducing zinc bis(imino-bis-carbimic acid methyl ester) in >10 portions at a time over a period of from 4 to 10 hours. In this manner, the exothermic reaction can be carried out safely and without any problems.

After the zinc bis(imino-bis-carbimic acid methyl ester) has been introduced, stirring is continued, preferably at 40° C. for 4 to 16 hours and at 80° C. for one hour.

Even though acetic anhydride is employed in stoichiometric amounts, the yields are surprisingly very high, about 85 to 95%.

Following reaction step b), the byproducts formed in steps a) and b) are separated off. Thus, for example, the zinc acetate formed in the acetylation is removed from the reaction solution and can preferably be washed with acetic acid and dried under reduced pressure at about 100° C. Here, the zinc acetate is obtained in virtually quantitative yield and can be reused without any problems in step a).

The acetic acid formed in the acetylation is preferably separated off by vacuum distillation, and it has been found to be particularly advantageous to carry out this vacuum distillation at a pressure of <100 mbar and a temperature of <90° C. If methanol-moist zinc bis(imino-bis-carbimic acid methyl ester) has been employed, in addition to acetic acid, methyl acetate is formed too, which can also be removed by distillation, together with the acetic acid.

For carrying out reaction step c), the 2,4-dimethoxy-6-methyl-1,3,5-triazine obtained after the distillative removal of byproducts is dissolved in methanol. Here, preference is given to preparing a 30 to 50% by weight strength solution requiring from 0.8 to 1.5 parts by weight of methanol per part by weight of the zinc bis(imino-bis-carbimic acid methyl ester ) employed in reaction step b). For carrying out reaction step c), the methanolic solution of 2,4-dimethoxy-6-methyl-1,3,5-triazine is preferably neutralized at a temperature of from 5 to 15° C. using an aqueous solution of methylamine (from 40 to 50% by weight), with, in particular, a pH of from 6.5 to 7.5 being set.

The neutralized methanolic solution is then reacted with further amounts of an aqueous solution of methylamine at from 10 to 30° C., preferably at from 10 to 15° C. Here, the methylamine can be employed in stoichiometric amounts, i.e. in equimolar amounts, or else in a large excess. Preferably, from 0.8 to 2 mol of methylamine are employed per mol of 2,4-dimethoxy-6-methyl-1,3,5-triazine. In this manner, 2-methoxy-4-methyl-6-methylamino-1,3,5-triazine is prepared in surprisingly very high yields of from 85 to 95%. Moreover, the corresponding end product is obtained in crystaine and readily filterable form and can be subsequently washed, if appropriate, with a dilute aqueous solution of methylamine, thus giving a virtually zinc-free product (zinc content<50 ppm).

In the context of the present invention, it is furthermore possible to subject the crude product obtained in step c) to a further purification where, according to a further embodiment, the crude product is subsequently treated with water at temperatures of from 80 to 100° C. Here, the product is preferably heated under gentle reflux with a twofold to fourfold excess of water. According to a further process variant, this subsequent treatment can be carried out in the presence of a surfactant, in particular a wetting agent, which is preferably employed in an amount of from 0.05 to 1% by weight, based on the amount of the aqueous solution. Following the treatment with water, which usually takes 5 to 6 hours, a pH of from 3.5 to 4.5 is set, preferably using acetic acid, the high-purity 2-methoxy-4-methyl-6-methylamino-1,3,5-triazine is isolated and dried, preferably under reduced pressure at from 10 to 200 mbar and at from 70 to 85° C. According to a further preferred embodiment, drying can also be carried out in a rotary dryer at from 20 to 100 mbar and about 80° C.

The end product dried in this manner has usually a residual water content of from 0.1 to 0.3% by weight. It is not possible to reduce this value noticeably, not even by prolonging the drying time, since the water is bound to the crystals. It is not possible to increase the temperature, since the end product has a strong tendency to sublime at temperatures exceeding 80° C.

Since a product having a particularly low water content is required for particular applications, for example for the preparation of sulfonylurea herbicides, the 2-methoxy-4-methyl-6-methylamino-1,3,5-triazine, which has already been dried, in the context of the present invention can be subjected to further treatment with excess methanol (onefold to sevenfold excess) at a preferred temperature of from 40 to 70° C., followed by removal of the methanol, for example by distillation, and, finally, drying of the residue. This drying is preferably carried out in a rotary dryer at a pressure of from 100 to 150 mbar and at about 80° C., it being possible to reduce the water content to about 50 to 500 ppm.

Thus, using the process according to the invention, it is possible to prepare 2-methoxy-4-methyl-6-methylamino-1,3,5-triazine in very high yields even without using zinc dicyanamide, it furthermore being possible to obtain a high-purity and virtually anhydrous product. Since the process can be carried out without any problems, it is furthermore highly suitable for use on an industrial scale.

DETAILED DESCRIPTION OF THE INVENTION

The examples below are meant to illustrate the present invention in more detail.

EXAMPLES

Example 1

Preparation of Zinc bis(imino-bis-carbimic Acid Methyl Ester)

In a stirred vessel, 859 g of 98% pure sodium dicyanamide are suspended in 4940 g of methanol. 95 g of zinc acetate are then added, and the reaction mixture is heated to reflux temperature. Once the reflux temperature has been reached, 8 portions of in each case 96 g of zinc acetate are introduced into the boiling reaction mixture, at intervals of in each case one hour. After the addition of zinc acetate has ended, heating under reflux is continued for 10 hours. The reaction mixture is then cooled and stirred for another 6 hours with water-cooling. The precipitate is then removed by centrifugation. This gives 1100 g of methanol-moist product (yield about 68%) having a moisture content of 5% by weight of methanol.

Example 2

Preparation of 2,4-dimethoxy-6-methyl-1,3,5-triazine 3035 g of acetic anhydride are initially charged in a stirred vessel, and 2184 g of methanol-moist 95% pure zinc bis(imino-bis-carbimic acid methyl ester) are then introduced in 28 portions at a time at from 38 to 40° C. and with efficient stirring, over a period of 7 hours. After the addition of zinc bis(imino-bis-carbimic acid methyl ester) has ended, stirring is continued at 40° C. for another 16 hours. The mixture is then heated to 80° C. over a period of one hour and stirred at this temperature for 2 hours. The reaction mixture is then cooled and stirred for about another 4 hours with water-cooling. The zinc acetate formed is filtered off with suction and washed on a nutsch filter using 4×300 g of acetic acid. The combined acetic-acid filtrates are then charged to a distillation apparatus, to remove distillatively a mixture of acetic acid and methyl acetate (ratio: about 80:20) under a reduced pressure of about 100 mbar. Once the main fraction of this mixture has been distilled off, the internal temperature is increased to 90° C. Following distillative removal of the remaining acetic acid, the mixture is finally cooled to about 30° C., and 2460 g of methanol are added to the product. This gives 4450 g of an about 40% by weight strength methanolic solution of 2,4-dimethoxy-6-methyl-1,3,5-triazine (yield: about 90%).

Example 3

Preparation of 2-methoxy-4-methyl-6-methylamino-1,3,5-triazine (Crude Product)

5000 g of a 40% by weight strength methanolic solution of 2,4-dimethoxy-6-methyl-1,3,5-triazine are initially charged and then, at from 5 to 10° C., admixed with a 40% by weight strength aqueous methylamine solution to neutralize the acetic acid, establishing a pH of from 7.2 to 7.5 (glass electrode). At from 13 to 15° C., 1500 g of a 40% by weight strength aqueous methylamine solution are then introduced over a period of 8 hours. After the addition of the methylamine solution has ended, stirring is continued at 14° C. for another 4 hours and then with water-cooling for 12 hours. The reaction product is subsequently filtered off with suction using a nutsch filter and washed with 5×900 ml of a 2% by weight strength methylamine solution and finally with 4×900 ml of water. The yield of 2-methoxy-4-methyl-6-methylamino-1,3,5-triazine, based on the dried product, is 1850 g (yield: about 93%).

Example 4

Purification of 2-methoxy-4-methyl-6-methylamino-1,3,5-triazine

The moist crude product of Example 3 is suspended in 7 l of water. 2 g of a nonionic wetting agent (Genapol 0X80 from Hoechst) are added, and the reaction mixture is then heated under gentle reflux and with efficient stirring for 6 hours. After cooling, the pH is adjusted to 3.7 by adding acetic acid, and stirring is then continued at 15° C. for one more hour. The solid is then filtered off with suction using a nutsch filter and washed with 4 l of water. Drying under reduced pressure at 80° C. gives 1720 g (yield: about 93%) of highly pure 2-methoxy-4-methyl-6-methylamino-1,3,5-triazine.

Content (HPLC): 99.8%.
Sum of all organic impurities (HPLC): <0.1%
Water (KF): 0.21%

Example 5

Preparation of Anhydrous 2-methoxy-4-methyl-6-methylamino-1,3,5-triazine 100 g of pure dried product having a water content of 0.21% are suspended in 350 g of methanol. The methanol is then distilled off at atmospheric pressure using a rotary evaporator. The residue is once more admixed with 350 g of methanol and is then distilled off using a rotary evaporator. The residue is finally dried under water pump vacuum at 80° C. This gives 99.7 g of 2-methoxy-4-methyl-6-methylamino-1,3,5-triazine having a water content of 50 ppm (KF) (yield: 100%).

What is claimed is:

1. A process of preparing 2-methoxy-4-methyl-6-methylamino-1,3,5 triazine comprising the steps of:
   a) reacting sodium dicyanamide with zinc acetate in methanol to prepare zinc bis(imino-bis-carbimic acid methyl ester),
   b) reacting the zinc bis(imino-bis-carbimic acid methyl ester) in dried or methanol moist form from step a) with acetic anhydride at from 30 to 80° C without addition of a solvent to give 2,4-dimethoxy-6-methyl-1,3,5 triazine, and
   c) removing any byproducts formed in step a) or b) and reacting the 2,4-dimethoxy-6-methyl-1,3,5-triazine, formed in step b), with methylamine in a methanolic solution at from 0 to 30° C to give 2-methoxy-4-methyl-6-methylamino-1,3,5-triazine.

2. The process as claimed in claim 1, wherein sodium dicyanamide and zinc acetate are employed in a molar ratio of from 2:1 to 2.1:1.

3. The process as claimed in claim 1, wherein step a) is carried out at temperatures from 40 to 70° C.

4. The process as claimed in claim 1, wherein from 4.0 to 4.4 mol of acetic anhydride are employed per mol of zinc bis(imino-bis-carbimic acid methyl ester).

5. The process as claimed in claim 1, wherein the zinc bis(imino bis-carbimic acid methyl ester) is in methanol moist from and has a methanol content of from 1 to 10% by weight and one mole of acetic anhydride is used per mol of methanol in the methanol-moist zinc bis(imino bis-carbimic acid methyl ester) in methanol moist form.

6. The process as claimed in claim 1, wherein the acetic anhydride of step b) is initially charged and the zinc bis(imino-bis-carbimic acid methyl ester) is reacted with the acetic anhydride in >10 portions over a period of from 4 to 6 hours.

7. The process of as claimed in claim 1, wherein zinc acetate formed in step b) is separated off and reused, if appropriate after washing with acetic acid.

8. The process as claimed in caim 1, wherein the acetic acid and, if present the methyl acetate formed in step b) is separated off before performing step c).

9. The process as claimed in claim 1, wherein step c) is carried out in the methanolic solution at a concentration of from 30 to 50% by weight.

10. The process as claimed in claim 9, wherein the methanolic solution of 2,4-dimethoxy-6-methyl-1,3,5-triazine is adjusted to a pH of from 6.5 to 7.5 using an aqueous solution of methylamine.

11. The process of as claimed in claim 1, wherein in step c), from 0.8 to 2 mol of methylamine are employed per mol of 2,4-dimethoxy-6-methyl-1,3,5-triazine.

12. The process as claimed in claim 11, wherein step c) is carried out at a temperature of from 10 to 15° C.

13. The process as claimed in claim 1, further comprising the step of washing the 2-methoxy-4-methyl-6-methylamino-1,3,5-triazine formed in step c) with a dilute aqueous solution of methylamine.

14. The process as claimed in claim 1, further comprising the step of treating the 2-methoxy-4-methyl-6-methylamino-1,3,5-triazine formed in step c) with water at temperatures of from 80 to 100° C.

15. The process as claimed in claim 14, wherein the subsequent treatment with water is carried out in the presence of from 0.05 to 1% by weight of a surfactant, in particular a wetting agent, based on the weight of the aqueous solution.

16. The process as claimed in claim 1, further comprising the step of reducing the water content of the 2-methoxy-4-methyl-6-methylamino-1,3,5-triazine produced in step c) to values of from 50 to 500 ppm by, (i) treating the 2-methoxy-4-methyl-6-methylamino-1,3,5-triazine with methanol, and then (ii) drying the 2-methoxy-4-methyl-6-methylamino-1,3,5-triazine.

17. The process as claimed in claim 16, wherein the methanol treatment is carried out at a temperature of from 40 to 70° C.

18. The process as claimed in claim 16, wherein drying after the treatment with methanol is carried out in a rotary dryer.

19. A process for preparing 2-methoxy-4-methyl-6-methylamino-1,3,5-triazine comprising the steps of:

a) reacting zinc bis(imino-bis-carbimic acid methyl ester) with acetic anhydride to give 2,4-dimethoxy-6-methyl-1,3,5-triazine; and b) reacting the 2,4-dimethoxy-6-methyl-1,3,5-triazine, formed in step a), with methylamine to give 2-methoxy-4-methyl-6-methylamino-1,3,5-triazine.

20. A process for preparing 2-methoxy-4-methyl-6-methylamino-1,3,5-triazine comprising the steps of:

a) reacting sodium dicyanamide with zinc acetate in methanol to form zinc bis(imino-bis-carbimic acid methyl ester), b) reacting the zinc bis(imino-bis-carbimic acid methyl ester) of step a) with acetic anhydride to form 2,4-dimethoxy-6-methyl-1,3,5-triazine, and c) reacting the 2,4-dimethoxy-6-methyl-1,3,5-triazine, formed in step b), with methylamine to form 2-methoxy-4-methyl-6-methylamino-1,3,5-triazine.

* * * * *